(12) United States Patent
Foster et al.

(10) Patent No.: US 10,132,739 B2
(45) Date of Patent: Nov. 20, 2018

(54) PARTICLE MANIPULATION SYSTEM WITH OUT-OF-PLANE CHANNEL AND RECOVERY ALGORITHM

(71) Applicant: Owl biomedical, Inc., Goleta, CA (US)

(72) Inventors: John Stuart Foster, Santa Barbara, CA (US); Kevin Eugene Shields, Santa Barbara, CA (US); Mark Naivar, Goleta, CA (US); Mehran Rajaian Hoonejani, Goleta, CA (US)

(73) Assignee: Owl biomedical, Inc., Goleta, CA (US)

( * ) Notice: Subject to any disclaimer, the term of this patent is extended or adjusted under 35 U.S.C. 154(b) by 0 days.

(21) Appl. No.: 15/159,841

(22) Filed: May 20, 2016

(65) Prior Publication Data
US 2016/0377526 A1    Dec. 29, 2016

Related U.S. Application Data

(63) Continuation-in-part of application No. 13/998,095, filed on Oct. 1, 2013, now Pat. No. 9,372,144.

(51) Int. Cl.
*G01N 15/14* (2006.01)
*B01L 3/00* (2006.01)
(Continued)

(52) U.S. Cl.
CPC .... *G01N 15/1484* (2013.01); *B01L 3/502715* (2013.01); *B01L 3/502738* (2013.01);
(Continued)

(58) Field of Classification Search
CPC ....... G01N 15/1484; G01N 2015/1068; G01N 15/1404; G01N 2015/1006; G01N 2015/149; F16K 99/0046; B01L 3/502738; B01L 3/502715; B01L 3/502761; B01L 2200/143; B01L 2400/043; B01L 2400/0633; B01L 2400/0622;
(Continued)

(56) References Cited

U.S. PATENT DOCUMENTS

| 6,431,212 B1* | 8/2002 | Hayenga | B01D 11/00 137/855 |
| 6,767,706 B2* | 7/2004 | Quake | B01F 5/0646 435/287.2 |

(Continued)

*Primary Examiner* — Samuel P Siefke
(74) *Attorney, Agent, or Firm* — Jaquelin K. Spong

(57) ABSTRACT

A particle manipulation system uses a MEMS-based, microfabricated particle manipulation device which has an inlet channel, output channels, and a movable member formed on a substrate. The movable member moves parallel to the fabrication plane, as does fluid flowing in the inlet channel. The movable member separates a target particle from the rest of the particles, diverting it into an output channel. However, at least one output channel is not parallel to the fabrication plane. The device may be used to separate a target particle from non-target material in a sample stream. In the event that the microfabricated particle manipulation device malfunctions as a result of a particle of debris becoming lodged in the microfabricated particle manipulation device, the system may invoke a recovery algorithm, that includes vibrating the microfabricated particle manipulation device using a pulse train at a frequency near its mechanical resonance.

20 Claims, 13 Drawing Sheets

(51) Int. Cl.
*F16K 99/00* (2006.01)
*G01N 15/10* (2006.01)

(52) U.S. Cl.
CPC .... *B01L 3/502761* (2013.01); *F16K 99/0046* (2013.01); *G01N 15/1404* (2013.01); *B01L 2200/0652* (2013.01); *B01L 2200/143* (2013.01); *B01L 2300/0627* (2013.01); *B01L 2300/0654* (2013.01); *B01L 2300/0864* (2013.01); *B01L 2400/043* (2013.01); *B01L 2400/0622* (2013.01); *B01L 2400/0633* (2013.01); *G01N 2015/1006* (2013.01); *G01N 2015/1068* (2013.01); *G01N 2015/149* (2013.01)

(58) Field of Classification Search
CPC ..... B01L 2300/0864; B01L 2300/0654; B01L 2300/0627; B01L 2200/0652
See application file for complete search history.

(56) References Cited

U.S. PATENT DOCUMENTS

| | | |
|---|---|---|
| 2001/0055812 A1 | 12/2001 | Mian |
| 2003/0175980 A1* | 9/2003 | Hayenga ............ B01L 3/502738 436/63 |
| 2005/0274672 A1* | 12/2005 | Tu ....................... A61M 1/3496 210/645 |
| 2007/0178529 A1 | 8/2007 | Breidford |
| 2007/0215528 A1* | 9/2007 | Hayenga ............ B01L 3/502761 209/576 |
| 2010/0225913 A1 | 9/2010 | Trainer |
| 2012/0122084 A1 | 5/2012 | Wagner et al. |
| 2012/0190105 A1 | 7/2012 | Foster et al. |
| 2013/0083315 A1* | 4/2013 | Lo ............................ G01J 3/46 356/73 |
| 2015/0093817 A1 | 4/2015 | Foster et al. |

* cited by examiner

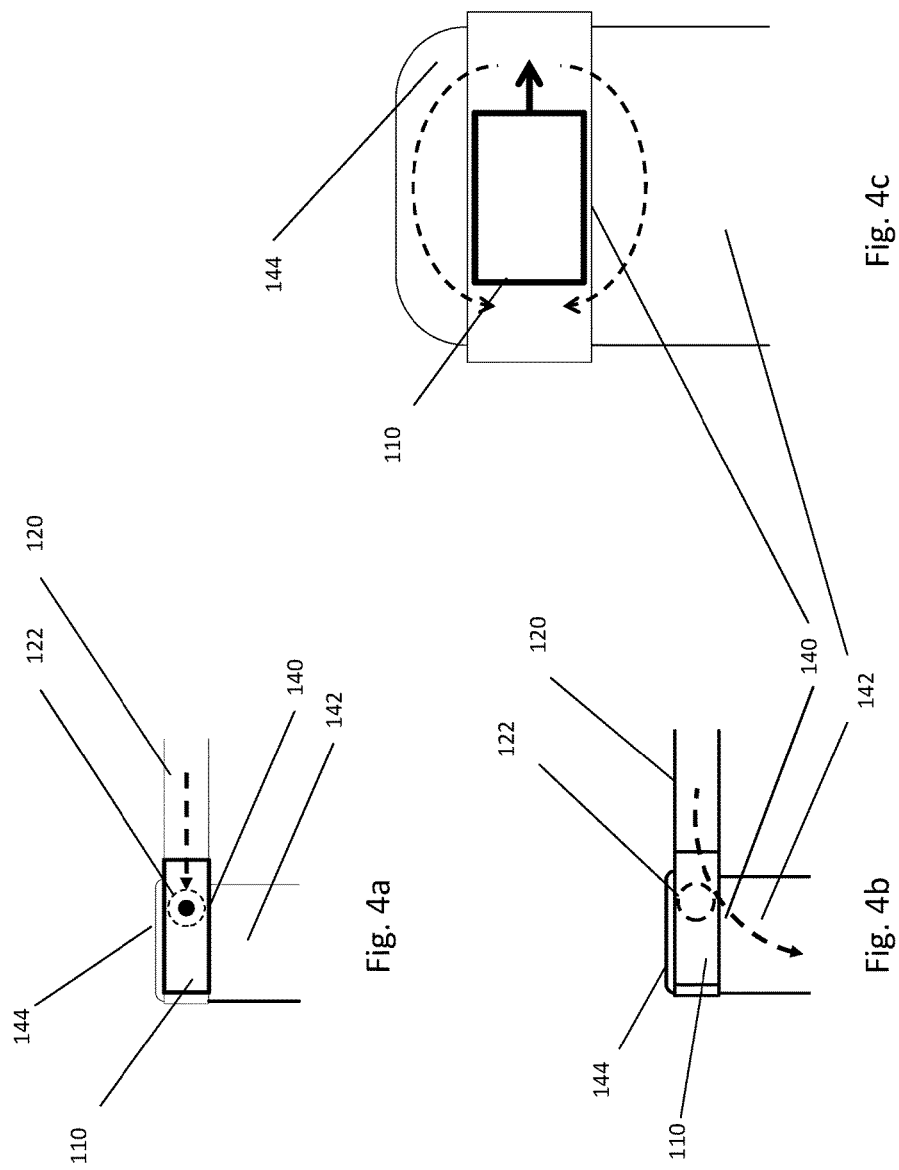

PARTICLE MANIPULATION SYSTEM WITH OUT-OF-PLANE CHANNEL AND RECOVERY ALGORITHM

CROSS REFERENCE TO RELATED APPLICATIONS

This US Patent Application is a continuation-in-part from U.S. patent application Ser. No. 13/998,095, filed Oct. 1, 2013. This application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particles passing by the MEMS device in a fluid stream.

In another example, a MEMS devices may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

SUMMARY

One feature of the MEMS-based microfabricated particle sorting system is that the fluid may be confined to small, microfabricated channels formed in a semiconductor substrate throughout the sorting process. The MEMS device may be a valve which separates one or more target particles from other components of a sample stream. The MEMS device may redirect the particle flow from one channel into another channel, when a signal indicates that a target particle is present. This signal may be photons from a fluorescent tag which is affixed to the target particles and excited by laser illumination in an interrogation region upstream of the MEMS device. Thus, the MEMS device may be a particle or cell sorter operating on a fluid sample confined to a microfabricated fluidic channel, but using detection means similar to a FACS flow cytometer. In particular, the '898 application discloses a microfabricated fluidic valve wherein the inlet channel, sort channel and waste channel all flow in a plane parallel to the fabrication plane of the microfabricated fluidic valve.

A substantial improvement may be made over the prior art devices by having at least one of the microfabricated fluidic channels route the flow out of the plane of fabrication of the microfabricated particle sorting device. A microfabricated particle sorting device with such an architecture has the advantage that the pressure resisting the valve movement is minimized when the valve opens or closes, because the movable member is not required to move a column of fluid out of the way. Instead, the fluid containing the non-target particles may move over and under the movable member to reach the waste channel. Furthermore, the force-generating apparatus may be disposed closer to the movable valve, resulting in higher forces and faster actuation speeds. As a result, the time required to open or close the valve may be much shorter than the prior art valve, improving sorting speed and accuracy. The systems and methods disclosed here may describe such a microfabricated particle sorting device with at least one out-of-plane channel. However, because of the small size of the features used in such a device, clogging of the valve or the channels by small pieces of debris may become a problem. Accordingly, in the systems and methods disclosed here, the device may monitor its own functioning, and invoke a recovery algorithm if a clog is detected.

In general, the system may include a microfabricated particle sorting device, a detecting device that generates a signal indicating that a malfunction has occurred, and a controller that invokes a recovery algorithm upon receiving the signal, wherein the recovery algorithm includes generating a plurality of pulses that vibrate the particle sorting device. Exemplary embodiments of these components are described in detail below.

Finally, the systems and methods disclosed herein, because they include microfabricated channels as well as the novel microfabricated particle sorting device design, may allow additional useful features to be implemented. For example, the techniques may form a particle manipulation system with cytometric capability, as described in co-pending U.S. patent application Ser. No. 13/507,830 (Owl-Cytometer) filed Aug. 1, 2012 and assigned to the same assignee as the present application. This patent application is incorporated by reference in its entirety. The MEMS device describe here may be used to manipulate the particles in the fluid stream enclosed in the microfabricated channel, while a plurality of interrogation regions also exist which may provide feedback on the manipulation. For example, in the case of cell sorting, one optical interrogation region may exist upstream of the MEMS device, and at least one additional optical interrogation region may exist downstream of the MEMS device, to confirm the results of the particle manipulation, that the correct cell has been sorted.

In another embodiment, the novel microfabricated particle sorting device architecture may make use of hydrodynamic particle focusing techniques, as taught by, for example, "Single-layer planar on-chip flow cytometer using microfluidic drifting based three-dimensional (3D) hydrodynamic focusing," by Xaiole Mao, et al. (hereinafter "Mao," Journal of Royal Society of Chemistry, Lab Chip, 2009, 9, 1583-1589). The microfabricated architecture of the systems and methods disclosed herein make them especially suitable for the techniques disclosed in Mao, as described further in U.S. patent application Ser. No. 13/998,096, (the '096 application) filed Oct. 1, 2013 and assigned to the same assignee as the present application. The '096 application is also incorporated by reference in its entirety.

These and other features and advantages are described in, or are apparent from, the following detailed description.

BRIEF DESCRIPTION OF THE DRAWINGS

Various exemplary details are described with reference to the following figures, wherein:

FIG. 4a is a simplified cross sectional view of a microfabricated particle sorting system in the actuated (sort) position, showing the flow of the sample stream into the sort channel which is in the same plane as the inlet channel; FIG. 4b is a simplified cross sectional view of a microfabricated particle sorting system in the quiescent (no sort) position, showing the flow of the sample stream into the waste channel which is not in the same plane as the inlet channel;

FIG. 4c is a simplified cross sectional view of a microfabricated particle sorting system in the quiescent (no sort) position, showing the flow of the sample stream into the waste channel which is not in the same plane as the inlet channel, wherein the sample stream flows around the top and the bottom of the diverter;

It should be understood that the drawings are not necessarily to scale, and that like numbers may refer to like features.

DETAILED DESCRIPTION

The system described herein is a particle sorting system which may make use of the microchannel architecture of a MEMS particle manipulation system. More generally, the systems and methods describe a particle manipulation system with an inlet channel and a plurality of output channels, wherein at least one of the plurality of output channels is disposed in a different plane than the inlet channel. This architecture has some significant advantages relative to the prior art, and is described more fully in co-pending U.S. patent application Ser. No. 13/998,095, filed Oct. 1, 2013, and incorporated by reference in its entirety.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation. In particular, it should be understood that the designations "sort" and "waste" are interchangeable, as they only refer to different populations of particles, and which population is called the "target" or "sort" population is arbitrary. The terms "valve" and "movable member" are used interchangeably to denote the movable portion of a microfabricated particle sorting device, that can be used to separate a target particle from the remainder material in a sample stream.

Figure 1:
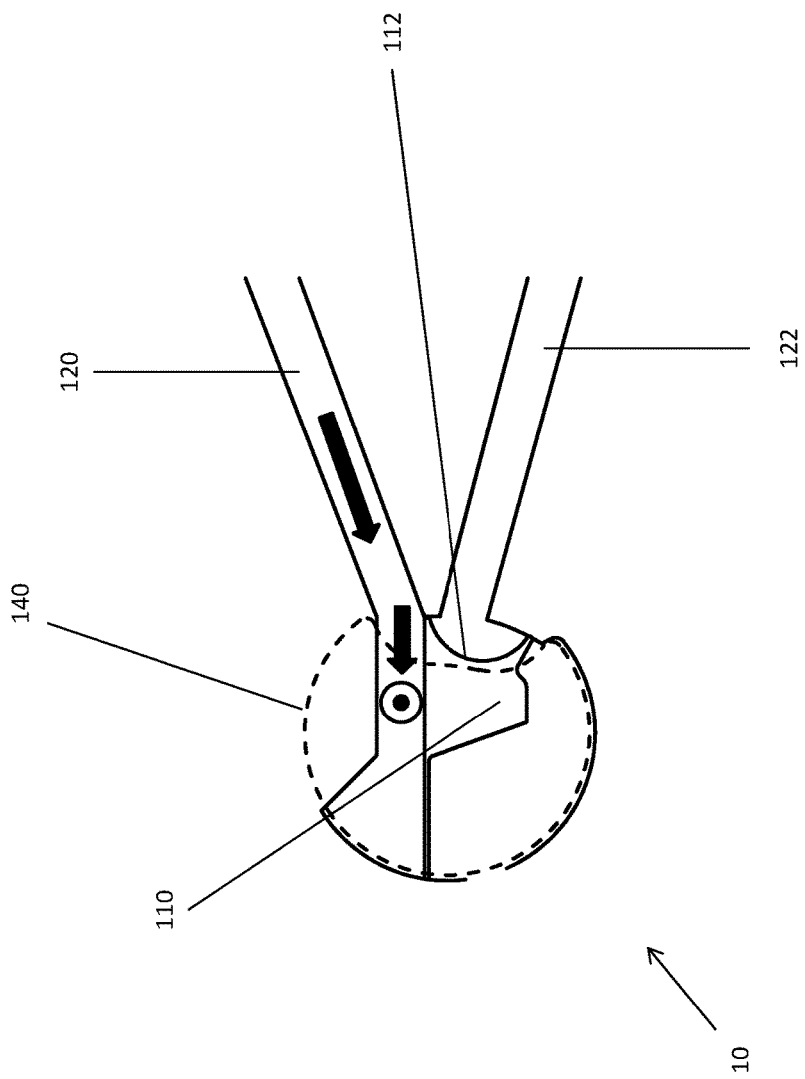
FIG. 1 is a simplified plan view of a microfabricated particle sorting system in the quiescent (no sort) position.

FIG. 1 is an plan view illustration of the novel microfabricated fluidic device 10 in the quiescent (un-actuated) position. The device 10 may include a microfabricated fluidic valve or movable member 110 and a number of microfabricated fluidic channels 120, 122 and 140. The fluidic microfabricated movable member 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves.

A sample stream may be introduced to the microfabricated fluidic movable member 110 by a sample inlet channel 120. The sample stream may contain a mixture of particles, including at least one desired, target particle and a number of other undesired, nontarget particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline. The inlet channel 120 may be formed in the same fabrication plane as the microfabricated valve or movable member 110, such that the flow of the fluid is substantially in that plane. The motion of the microfabricated valve or movable member 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature, and further discussed below with respect to FIG. 12. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the microfabricated valve 110 in the position shown, the input stream passes unimpeded to an output orifice and channel 140 which is out of the plane of the inlet channel 120, and thus out of the fabrication plane of the device 10. That is, the flow is from the inlet channel 120 to the output orifice 140, from which it flows substantially vertically, and thus orthogonally to the inlet channel 120. This output orifice 140 leads to an out-of-plane channel that may be perpendicular to the plane of the paper showing FIG. 1, and depicted in the cross sectional views of FIGS. 4a-4c. More generally, the output channel 140 is not parallel to the plane of the inlet channel 120 or sort channel 122, or the fabrication plane of the movable member 110.

The output orifice 140 may be a hole formed in the fabrication substrate, or in a covering substrate that is bonded to the fabrication substrate. A relieved area above and below the sorting valve or movable member 110 allows fluid to flow above and below the movable member 110 to output orifice 140, and shown in more detail in FIGS. 4a-4c. Further, the microfabricated valve 110 may have a curved diverting surface 112 which can redirect the flow of the input stream into a sort output stream, as described next with respect to FIG. 2. The contour of the orifice 140 may be such that it overlaps some, but not all, of the inlet channel 120 and sort channel 122. By having the contour 140 overlap the inlet channel, and with relieved areas described above, a route exists for the input stream to flow directly into the waste orifice 140 when the movable member or microfabricated valve 110 is in the un-actuated waste position.

Figure 2:
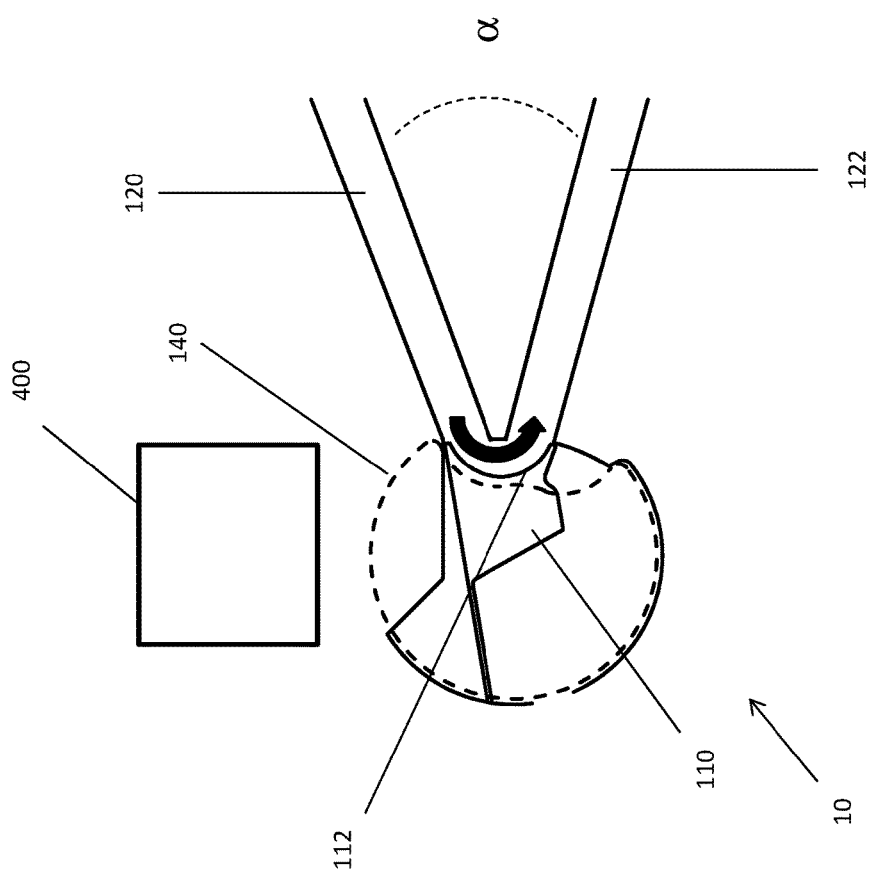
FIG. 2 is a simplified plan view of a microfabricated particle sorting system in the actuated (sort) position.

FIG. 2 is a plan view of the microfabricated device 10 in the actuated position. In this position, the movable member or microfabricated valve 110 is deflected upward into the position shown in FIG. 2. The diverting surface 112 is a sorting contour which redirects the flow of the inlet channel 120 into the sort output channel 122. The output channel 122 may lie in substantially the same plane as the inlet channel 120, such that the flow within the sort channel 122 is also in substantially the same plane as the flow within the inlet channel 120. There may be an angle α between the inlet channel 120 and the sort channel 122, This angle may be any value up to about 90 degrees. Actuation of movable member 110 may arise from a force from force-generating apparatus 400, shown generically in FIG. 2. In some embodiments, force-generating apparatus may be an electromagnet, however, it should be understood that force-generating apparatus may also be electrostatic, piezoelectric, or some other means to exert a force on movable member 110, causing it to move from a first position (FIG. 1) to a second position (FIG. 2).

More generally, the micromechanical particle manipulation device shown in FIGS. 1 and 2 may be formed on a surface of a fabrication substrate, wherein the micromechanical particle manipulation device may include a microfabricated, movable member 110 having a first diverting surface 112, wherein the movable member 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface, and a plurality of output channels 122, 140 into which the microfabricated member diverts the fluid, and wherein the flow in at least one of the output channels 140 is not parallel to the plane, and wherein at least one output channel 140 is located directly below at least a portion of the movable member 110 over at least a portion of its motion.

In one embodiment, the diverting surface 112 may be nearly tangent to the input flow direction as well as the sort output flow direction, and the slope may vary smoothly between these tangent lines. In this embodiment, the moving mass of the stream has a momentum which is smoothly shifted from the input direction to the output direction, and thus if the target particles are biological cells, a minimum of force is delivered to the particles. As shown in FIGS. 1 and 2, the micromechanical particle manipulation device 10 has a first diverting surface 112 with a smoothly curved shape, wherein the surface which is substantially tangent to the direction of flow in the sample inlet channel at one point on the shape and substantially tangent to the direction of flow of a first output channel at a second point on the shape, wherein the first diverting surface diverts flow from the sample inlet channel into the first output channel when the movable member 110 is in the first position, and allows the flow into a second output channel in the second position.

In other embodiments, the overall shape of the diverter 112 may be circular, triangular, trapezoidal, parabolic, or v-shaped for example, but the diverter serves in all cases to direct the flow from the inlet channel to another channel.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the microfabricated valve 110 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

Figure 3B:
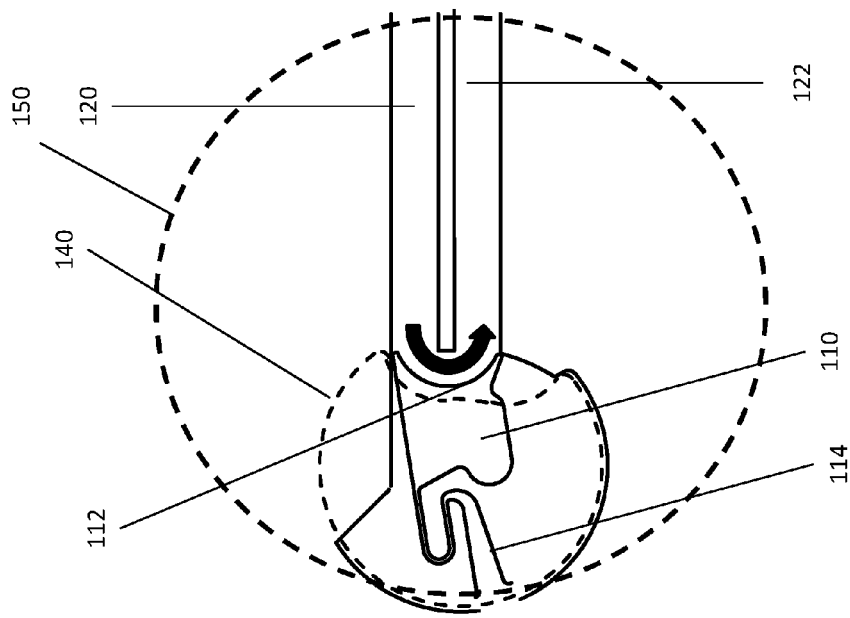
FIG. 3b is a simplified illustration of a microfabricated particle sorting system showing the field of view of the detector, with the microfluidic particle sorting device in the actuated (sort) position.
Figure 3A:
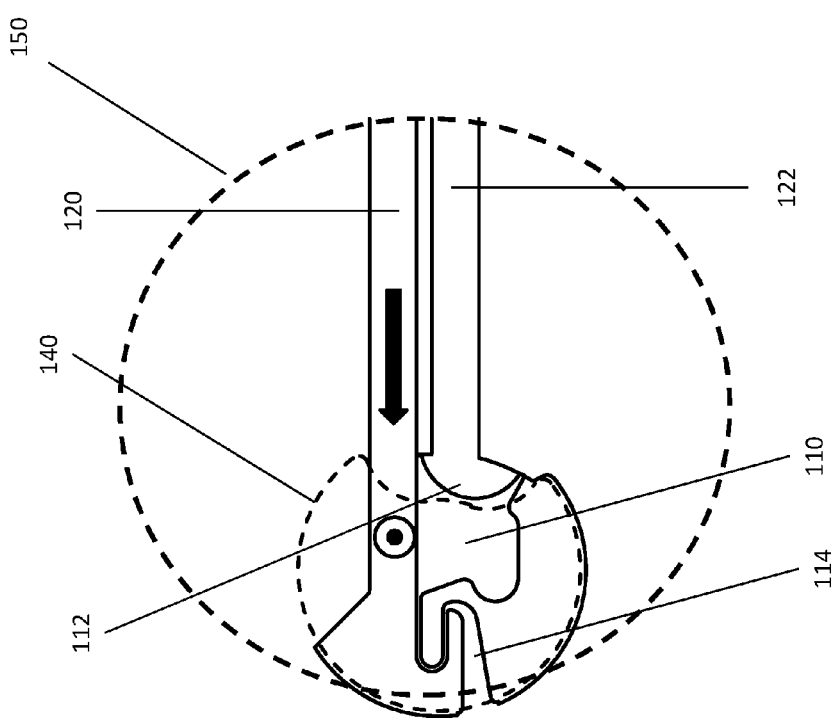
FIG. 3a is a simplified plan view of a microfabricated particle sorting system showing the field of view of the detector, with the microfluidic particle sorting device in the quiescent (no sort) position.

FIGS. 3a and 3b illustrate an embodiment wherein the angle α between the inlet channel 120 and the sort channel 122 is approximately zero degrees. Accordingly, the sort channel 122 is essentially antiparallel to the inlet channel 120, such that the flow is from right to left in the inlet channel 120. With microfabricated valve 110 in the un-actuated, quiescent position shown in FIG. 3a, the inlet stream flows straight to the waste orifice 140 and vertically out of the device 10.

In FIG. 3b, the microfabricated valve 110 is in the actuated, sort position. In this position, the flow is turned around by the diverting surface 112 of the microfabricated valve 110 and into the antiparallel sort channel 122. This configuration may have an advantage in that the field of view of the detector 150 covers both the inlet channel 120 and the sort channel 122. Thus a single set of detection optics may be used to detect the passage of a target particle through the respective channels. It may also be advantageous to minimize the distance between the detection region and the microfabricated valve 110, in order to minimize the timing uncertainty in the opening and closing of the microfabricated valve.

The movable member or microfabricated valve 110 may be attached to the substrate with a flexible spring 114. The spring may be a narrow isthmus of substrate material. In the example set forth above, the substrate material may be single crystal silicon, which is known for its outstanding mechanical properties, such as its strength, low residual stress and resistance to creep. With proper doping, the material can also be made to be sufficiently conductive so as to avoid charge build up on any portion of the device, which might otherwise interfere with its movement. The spring may have a serpentine shape as shown, having a width of about 1 micron to about 10 microns and a spring constant of between about 10 N/m and 100 N/m, and preferably about 40 N/m.

FIGS. 4a, 4b, 4c are cross sectional views illustrating the operation of the out-of-plane waste channel 140. FIG. 4c is slightly enlarged relative to FIGS. 4a and 4b, in order to show detail of the flow around the movable member 110 and into the waste channel 142 through waste orifice 140. In this embodiment, the waste channel 142 is vertical, substantially orthogonal to the inlet stream 120 and sort stream 122. It should be understood that other embodiments are possible other than orthogonal, but in any event, the flow into waste channel 142 is out of the plane of the flow in the inlet channel 120 and/or sort channel 122. As shown in FIG. 4a, with the microfabricated valve in the sort, actuated position, the inlet stream and target particle may flow into the sort stream, which in FIG. 4a is out of the paper, and the waste orifice 140 is largely, though not completely, blocked by the movable member 110. The area 144 (shown more clearly in FIG. 4c) on top of the valve or movable member 110 may be relieved to provide clearance for this flow.

When the microfabricated valve or movable member 110 is un-actuated as in FIG. 4b, the flow of the inlet channel 120 may flow directly into the waste channel 142 by going over, around or by the movable member or microfabricated valve 110. The area 144 on top of the microfabricated valve or movable member 110 may be relieved to provide clearance for this flow. The relieved area 144 is shown in greater detail in the enlarged FIG. 4c. Thus when the movable member is un-actuated, the flow will be sent directly to the waste channel. When the movable member is actuated, most of the fluid will be directed to the sort channel, although liquid may still flow over and under the movable member.

Thus, the purpose of providing flow both under and over the movable member 110 is to reduce the fluid pressure produced by the actuator motion in the region behind the microfabricated valve or movable member 110. In other words, the purpose is to provide as short a path as possible between the high pressure region in front of the microfabricated valve 110 and the low pressure region behind the microfabricated valve. This allows the microfabricated valve to operate with little pressure resisting its motion. As a result, the movable microfabricated valve 110 shown in FIGS. 1-4c may be substantially faster than microfabricated valves which have all channels disposed in the same plane.

Another advantage of the vertical waste channel 142 is that by positioning it directly underneath a stationary permeable feature 130 and movable permeable feature 116, the magnetic gap between the permeable features 116 and 130 can be narrower than if the fluidic channel went between them. The narrower gap enables higher forces and thus faster actuation compared to prior art designs. A description of the magnetic components and the magnetic actuation mechanism will be given next, and the advantages of the out-of-plane channel architecture will be apparent.

Figure 5:
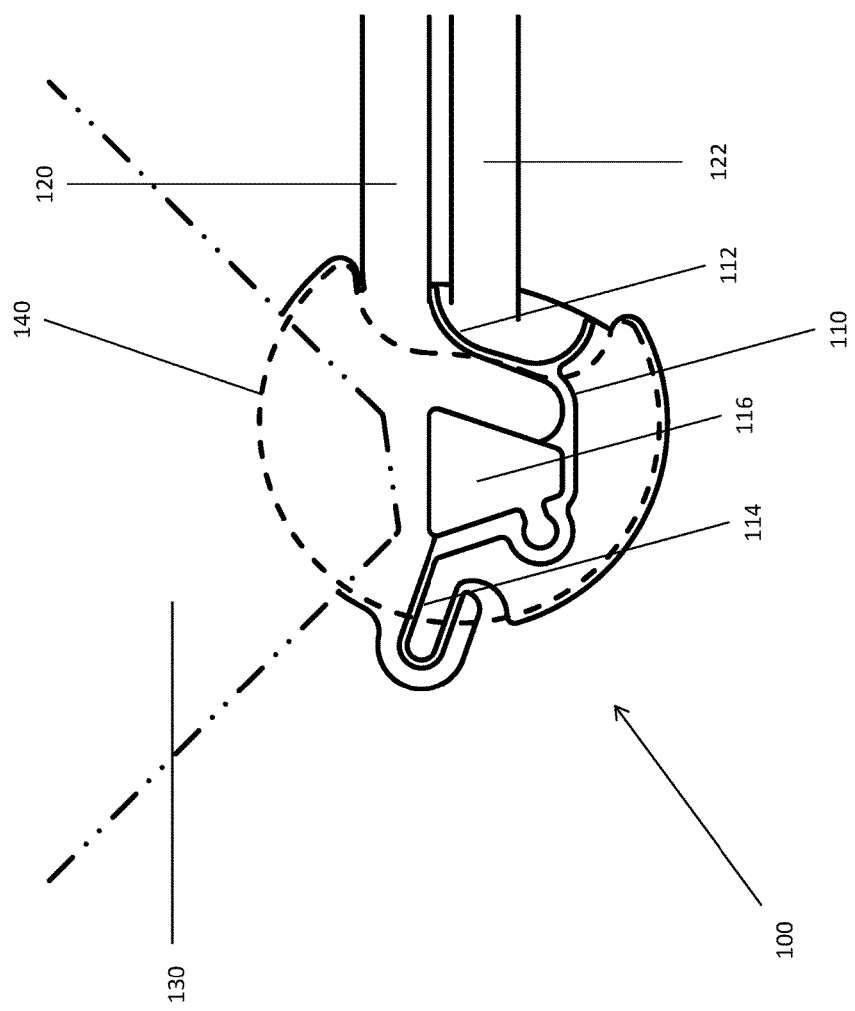
FIG. 5 is a simplified plan view of a microfabricated particle sorting system in the quiescent (no sort) position, showing the stationary magnetically permeable feature.

FIG. 5 is a plan view of another exemplary embodiment of device 100, showing the disposition of a stationary permeable feature 130 and further detail of the movable member 110. In this embodiment, the movable member 110 may include the diverting surface 112, the flexible hinge or spring 114, and a separate area 116 circumscribed but inside the line corresponding to movable member 110. This area 116 may be inlaid with a permeable magnetic material such as nickel-iron permalloy, and may function as described further below.

A magnetically permeable material should be understood to mean any material which is capable of supporting the formation of a magnetic field within itself. In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ $H \cdot m^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux.

Figure 6:
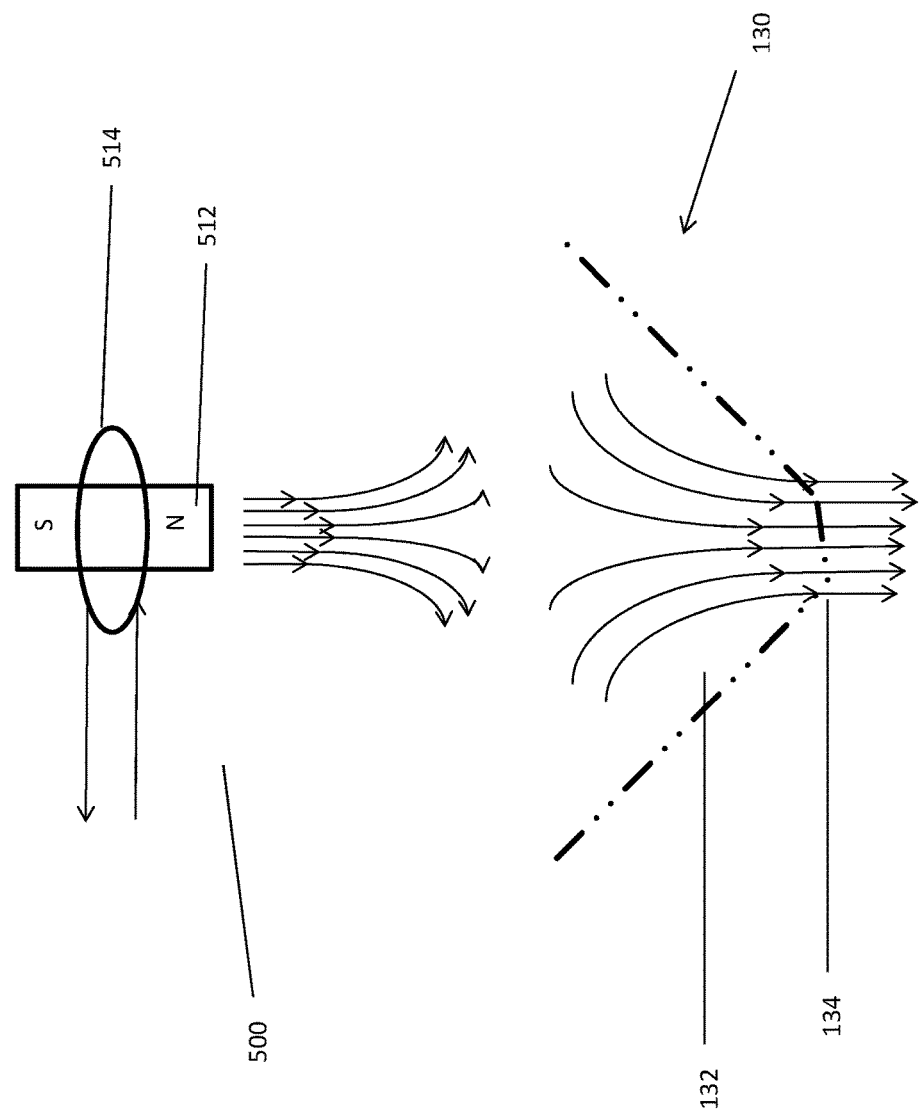
FIG. 6 is a plan view of the actuation mechanism for the microfabricated particle sorting system, showing the functioning of the external magnetic field in combination with the stationary magnetically permeable feature.
Figure 7:
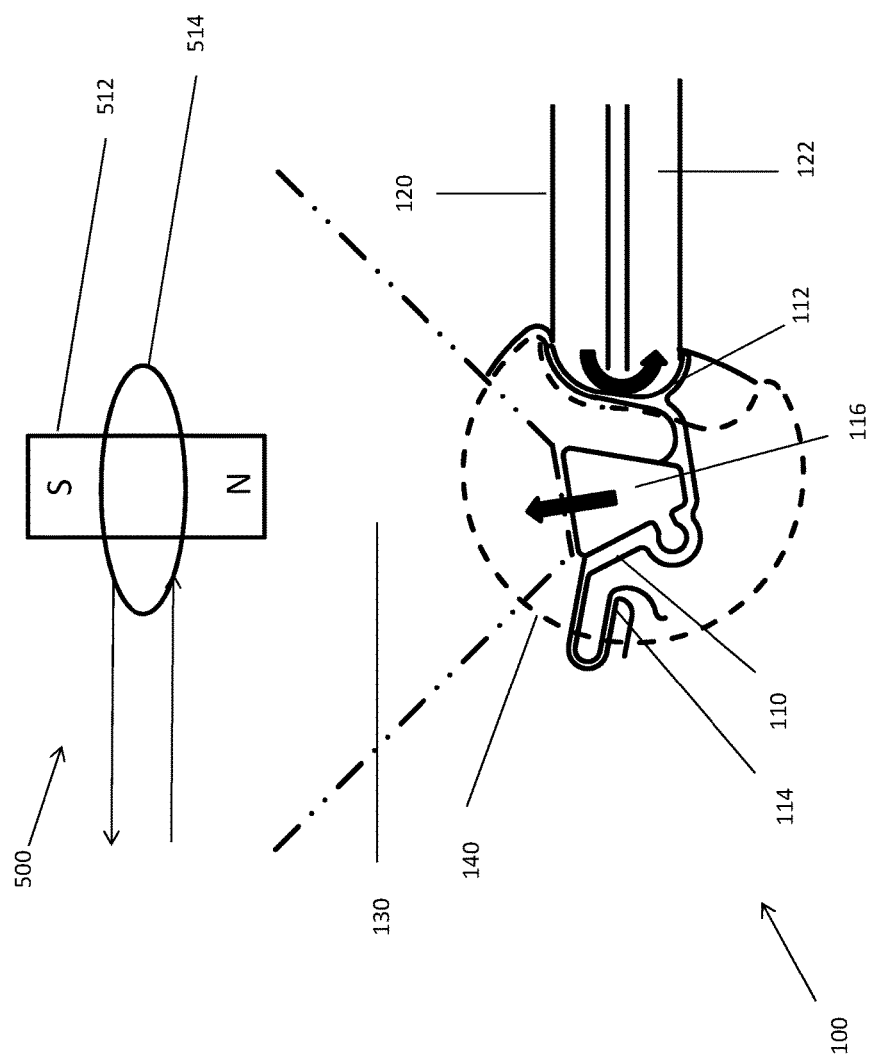
FIG. 7 is a plan view of the actuation mechanism for the microfabricated particle sorting system, showing the functioning of the external magnetic field in combination with the stationary magnetically permeable feature, in the actuated (sort) position.

An external source of magnetic field lines of flux may be provided outside the device 100, as shown in FIG. 6. This source may be an electromagnet 500. The electromagnet 500 may include a permeable core 512 around which a conductor 514 is wound. The wound conductor or coil 514 and core 512 generate a magnetic field which exits the pole of the magnet, diverges, and returns to the opposite pole, as is well known from electromagnetism. Accordingly, the movable member 110 is generally drawn toward the pole of the electromagnet 500 as shown in FIG. 7.

However, the performance of the device 100 can be improved by the use of a stationary permeable feature 130. The term "stationary feature" should be understood to mean a feature which is affixed to the substrate and does not move relative to the substrate, unlike movable member or microfabricated valve 110. A stationary permeable feature 130 may be shaped to collect these diverging lines of flux and refocus them in an area directly adjacent to the movable member 110 with inlaid permeable material. The stationary permeable feature may have an expansive region 132 with a narrower throat 134. The lines of flux are collected in the expansive region 132 and focused into and out of the narrow throat area 134. Accordingly, the density of flux lines in the throat area 134 is substantially higher than it would be in the absence of the stationary permeable feature 130. Thus, use of the stationary permeable feature 130 though optional, allows a higher force, faster actuation, and reduces the need for the electromagnet 500 to be in close proximity to the device 10. From the narrow throat area 134, the field lines exit the permeable material and return to the opposite magnetic pole of the electromagnet 500. But because of the high concentration of field lines in throat area 134, the permeable material 116 inlaid into movable member 110 may be drawn toward the stationary permeable feature 130, bringing the rest of movable member with it.

When the electromagnet is quiescent, and no current is being supplied to coil 514, the restoring force of spring 114 causes the movable member 110 to be in the "closed" or "waste" position. In this position, the inlet stream passes unimpeded through the device 100 to the waste channel 140. This position is shown in FIG. 5. When the electromagnet 500 is activated, and a current is applied through coil 514, a magnetic field arises in the core 512 and exits the pole of the core 512. These lines of flux are collected and focused by the stationary permeable feature 130 and focused in the region directly adjacent to the throat 134. As mentioned previously, the permeable portion 116 of the movable member 110 is drawn toward the throat 134, thus moving the movable member 110 and diverting surface 112 such that the inlet stream in inlet channel 120 is redirected to the output or sort channel 122. This position is shown in FIG. 7.

Permalloy may be used to create the permeable features 116 and 130, although it should be understood that other permeable materials may also be used. Permalloy is a well known material that lends itself to MEMS lithographic fabrication techniques. A method for making the permeable features 116 and 130 is described further below.

As mentioned previously, having the waste channel 140 and 142 directly beneath the movable member or microfabricated valve 110 allows the movable permeable feature 116 to be disposed much closer to the stationary permeable feature 130. If instead the waste channel were in the same plane, this gap would have to be at least large enough to accommodate the waste channel, along with associated tolerances. As a result, actuation forces are higher and valve opening and closing times are much shorter. This in turn corresponds to either faster sorting or better sorting accuracy, or both.

With the use of the electromagnetic actuation technique described above, actuation times on the order of 10 microseconds can be realized. Accordingly, the particle sorting device is capable of sorting particles at rates in excess of 50 kHz or higher, assuming 10 microseconds required to pull the actuator in, and 10 microseconds required to return it to the as-manufactured position.

As mentioned previously, the microfabricated particle manipulation device 100 makes use of microfabricated channels, which are formed in a substrate surface using lithographic techniques. Because these lithographic processes can create very fine features, the diameter of the channels may be quite small, on the order of about 50 microns in diameter. Accordingly, small pieces of foreign or unexpected debris may clog these microfabricated channels, and possibly jam the movable member 110 of the particle manipulation device 100. In particular, a piece of debris flowing down the input channel 120 may become wedged, or stuck, in the movable member 110, causing it to remain in the open or closed position. The situation is shown schematically in FIG. 8.

Figure 8:
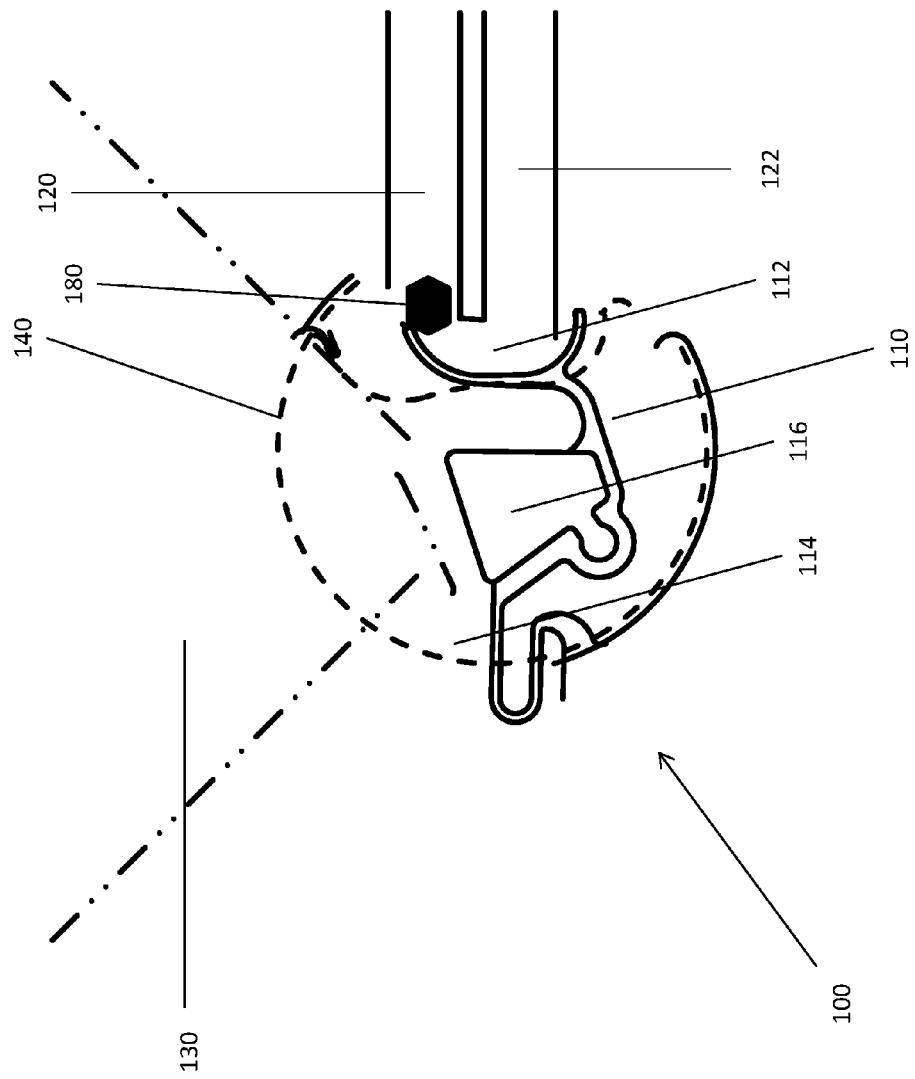
FIG. 8 is a simplified view of the microfabricated particle sorting system, wherein the microfabricated particle sorter has become jammed with debris.

FIG. 8 shows the permeable material 130, the inlaid material 116, the restoring spring 114, and the diverting surface 112. The sample stream flows through the input channel 120, to the movable member 110, and into the waste channel 140 if it does not contain the target particle. However, if a target particle is detected in the input channel 120, the controller may send a signal to the electromagnet 500 to rotate the movable member 110 to the sort position as was shown in FIGS. 3a and 3b. This rotation diverts the target particle from the input channel 120, into the sort channel, 122. Any small pieces of debris flowing in the sample stream may become wedged in the movable member 110, as it attempts to open or close.

As with the valves shown in FIGS. 1-7, this valve may include a microfabricated, movable member formed on the substrate, and having a first diverting surface, wherein the movable member moves from a first position to a second position in response to a force applied to the movable member, wherein the motion is substantially in a plane parallel to the surface of the substrate, an sample inlet channel formed in the substrate and through which a fluid flows, the fluid including at least one target particle and non-target material, wherein the flow in the sample inlet channel is substantially parallel to the surface, a plurality of output channels into which the microfabricated member diverts the fluid, and wherein the flow in at least one of the output channels is substantially orthogonal to the plane, and wherein at least one output channel is located directly below at least a portion of the microfabricated member over at least a portion of its motion.

The plurality of output channels may further comprise a sort channel and a waste channel, wherein flow in the sort channel is substantially antiparallel to flow in the sample inlet channel, and wherein flow in the waste channel is substantially orthogonal to flow in the sample inlet channel and the sort channel. The micromechanical particle manipulation device may also include a first permeable magnetic material inlaid in the movable member, a first stationary permeable magnetic feature disposed on the substrate, and a first source of magnetic flux external to the movable member and substrate on which the movable member is formed. The movable member may move from the first position to the second position when the source of magnetic flux is activated.

In any case, movable member 110 may no longer move in response to signals from the controller, as designed. In this event, the sorter may become wedged, or stuck in the open or closed position, such that it no longer accurately sorts target particles into the sort channel 122 and waste material into the waste channel 140. The result of this malfunction may be a loss of yield, loss of purity, or both.

When this situation arises, a method disclosed here for freeing the movable member 110, and returning the device to his previous performance, may be invoked. The method includes applying a plurality of pulses which are at or near a vibrational frequency of the particle manipulation device 100, to the electromagnet 500. This electromagnet 500 was shown schematically in FIG. 6. Accordingly, when it has been detected that the movable member 110 has become jammed, or locked, by debris, a high frequency pulse train may be sent to the electromagnetic coil 514 wound around the permeable core 512. This causes the electromagnet 500 to emit a magnetic field with a variable amplitude and frequency, which alternately pulls the permeable material 116 in the movable member 110 towards the core 512 and then releases it according to the spring constant of the spring 114. Accordingly, the movable member 110 will vibrate at a frequency determined by the frequency of the pulse train delivered to the electromagnet 500, and the mechanical resonance characteristics of the movable member 110 of the microfabricated particle manipulation device 100.

Accordingly, in the general case, the particle manipulation system may include a microfabricated valve, a detecting device that generates a signal indicating that a malfunction has occurred, and a controller that invokes a recovery algorithm upon receiving the signal, wherein the recovery algorithm includes generating a plurality of pulses that vibrate the particle sorting device. The plurality of pulses may comprise at least one of a series of square waves, sinusoids, trapezoid and ramps. The plurality of pulses may include at least one second pulse, which follows an initial pulse within about 50 microseconds of the initial pulse. The plurality of pulses may comprise a train of pulses with a range of frequencies.

If the frequency of this pulse train is chosen to be near the mechanical resonant frequency, the motion may be amplified by the resonance. This amplified resonant motion may be sufficient to dislodge the debris 180, or grind it to smaller particles which are then passed through the system. In any event, the movable member 110 may be freed by the application of this pulse train to the electromagnet 500. This constitutes a recovery algorithm invoked when a determination is made that the particle manipulation device 100 has malfunctioned Accordingly, the particle manipulation system may use a range of frequencies which includes a mechanical resonance frequency of the microfabricated particle sorting valve. The motion of the movable member may be amplified by resonant excitation by the plurality of pulses. The plurality of pulses may comprise a train of pulses with a range of frequencies beginning at a lower bound, and increasing in frequency to an upper bound, such that the pulse train is a chirp. The range of frequencies may also begin at an upper bound, and decrease in frequency to a lower bound, such that the pulse train is a descending chirp.

Figure 9:
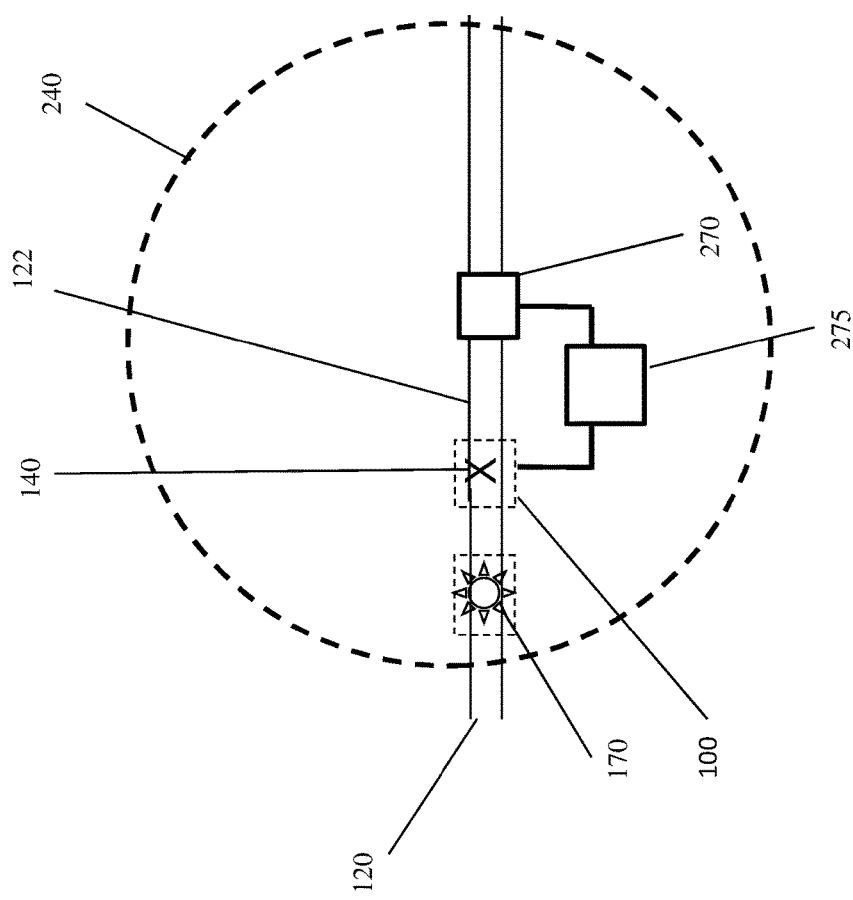
FIG. 9 is a simplified view of a microfabricated particle sorting system, having an implementation of the recovery algorithm.

A system for implementing this method for using a microfabricated particle sorting device is shown in FIG. 9. FIG. 9 is a qualitative plan view of the system for operating the microfabricated particle sorting device 10, 100 with recovery algorithm. Included in the system is an input channel 120, and interrogation region 170, a particle manipulation stage 100 a sort channel 122, and a malfunction detector 270. The malfunction detector 270 may detect the malfunction condition of the movable member 110 as described briefly above. The malfunction detector 270 may use any of a number of methodologies for detecting the malfunction of the movable member 110, as described below.

When the malfunction detector 270 detects the condition of a malfunction in the movable member 110, it may put out a signal to a controller 275 to invoke the recovery algorithm described here. Controller 275 may then send out a train of pulses to the electromagnet 500 which may drive the movable member 110 in vibration as described above. The quantitative and qualitative features of this recovery algorithm are described below with respect to the following FIGS. 11-13. In any case, the algorithm applied by the controller 275 to the movable member 110 may succeed and freeing the movable member 110 from its malfunction. At this point, the particle manipulation system 1000 may return to its functional state.

Figure 10:
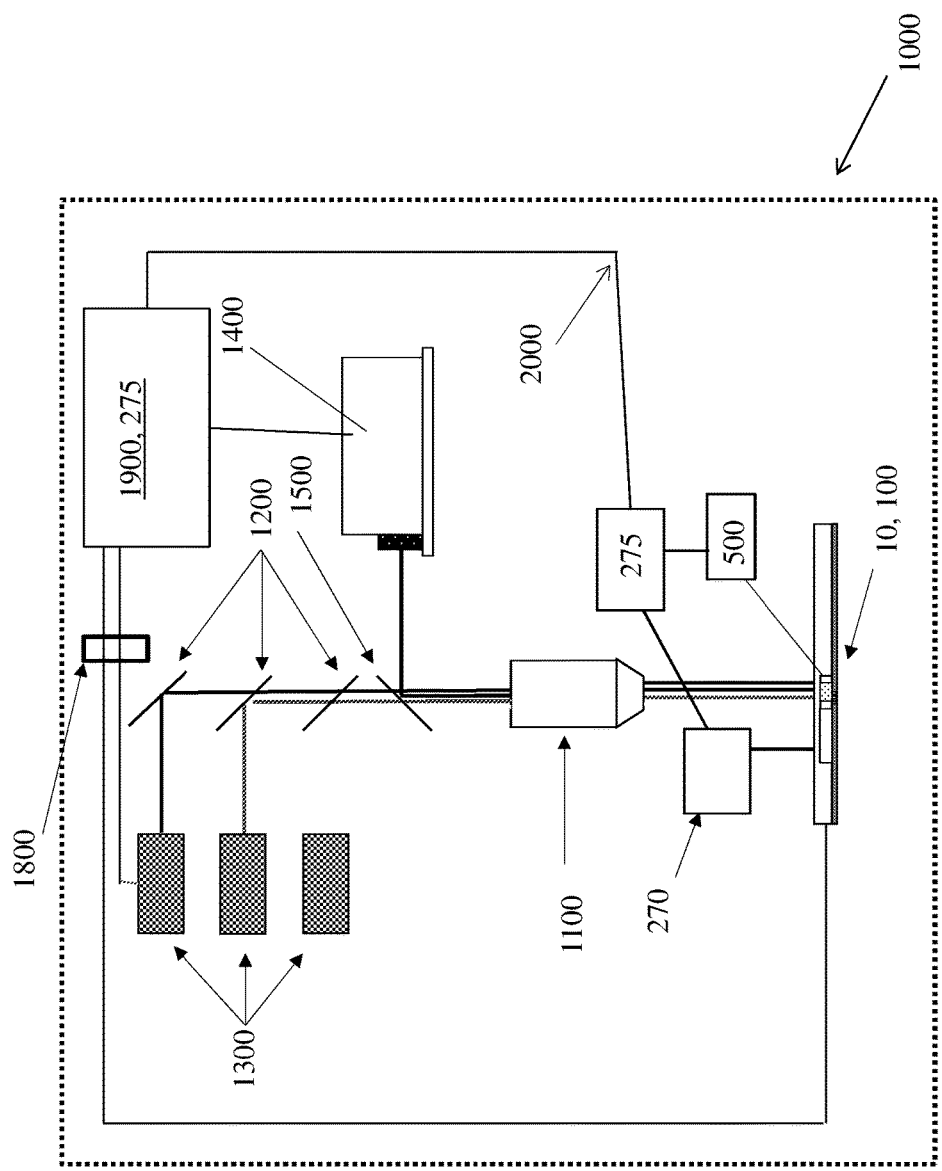
FIG. 10 is a system-level diagram of the microfabricated particle sorting system, with an implementation of the recovery algorithm.

The microfabricated particle manipulation device 10 or 100 with recovery algorithm may be used in a particle sorting system 1000 enclosed in a housing containing the components shown in FIG. 10. The MEMS particle manipulation devices 10 or 100 may be enclosed in a plastic, disposable cartridge which is inserted into the system 1000. The insertion area may be a movable stage with mechanisms available for fine positioning of the particle manipulation device 10 or 100 and associated microfluidic channels against one or more data, which orient and position the detection region and particle manipulation device 10 or 100 with respect to the collection optics 1100. If finer positioning is required, the inlet stage may also be a translation stage, which adjusts the positioning based on observation of the location of the movable member 110 relative to a datum.

It should be understood that although FIG. 10 shows a particle sorting system 1000 which uses a single laser source 1400, multiple light sources, multiple detection optics and multiple channels may also be used.

The embodiment shown in FIG. 10 is based on a FACS-type detection mechanism, wherein one or more lasers 1400 impinges on the sample inlet channel 120 as described above. The relative amount of light may be monitored by a computer 1900. The computer 1900 may then generate a control signal that controls the electromagnet 500. Upon receipt of a fluorescence signal from a target particle, the controller 1900 may output a sort trigger that caused the electromagnet 500 to be energized, thus moving the movable member 110 into the sort position shown in FIGS. 3a and 3b. The movable member thus diverts the target particle from the input channel 120 into the sort channel 122 rather than the waste channel 140. This is normal operation of the microfabrication particle sorting system 1000. However, when a malfunction is detected by detector 270, the recovery algorithm invoked by the controller 275.

The other optical components in particle manipulation system 1000 may include a beamsplitter 1500 and multiple color detectors 1300. The beam splitter 1500 may reflect the incoming light from laser 1400 onto the MEMS sorter 100, and pass the outgoing light reflected from the rear surface of the channel 120 to the turning mirrors 1200 and on to detectors 1300.

The output of detectors 1300 may be analyzed by the controller 1900 and compared to a threshold in normal operation.

Other sorts of components may be included in the system 1000, such as in electronic distinguishing means 1800 to separate the signals from multiple laser sources, for example. These components may include, for example, a signal filter, mixer, phase locked loop, multiplexer, trigger, or any other similar device that can separate or distinguish the signals. Component 1800 may also include a high pass and/or low pass electronic filter or the envelope detector. The multiple sets of signals from the electronic distinguishing means 1800 may be handled differently by the logic circuits 1900 in order to separate the signals.

In one embodiment, the MEMS particle manipulation system 1000 may be used in conjunction with one or more additional downstream laser interrogation regions, wherein the additional laser interrogation regions are used to confirm the effectiveness or accuracy of a manipulation stage in manipulating a stream of particles. The downstream evaluation from laser interrogation region 280 past the sorting stage 100 and 200 may allow the operator to measure one event number (e.g. the captured event rate post-sort) divided by another event number (e.g. the initial event rate pre-sort) for individual particle types, and to feedback to adjust initial interrogation parameters (e.g. such as x, y, z position and also "open window" length in time) based on this ratio. This method may be used to optimize the yield or accuracy of the system 1000.

Alternatively, the operator could measure the event rate post-sort of target cells, divided by total event rate post-sort feedback to adjust initial laser interrogation parameters such as x, y, z position and also "open window" length in time, in order to optimize the purity of the sorting system 1000. These sorting parameters may be adjusted by changing control signal 2000 which is sent by computer 1900 to electromagnet 500, or by changing the optical detection parameters or by changing the laser control signals, as shown in FIG. 10.

In any case, the MEMS particle manipulation system 1000 may have optimization procedures which may be automated, or implemented by an operator. The system 1000 may thereby be "self-aware" or self-monitoring. A sudden deviation of the performance of the MEMS particle manipulation system 1000 may be an indication of a malfunction. Accordingly, the controller 1900 may also serve as the detector 270. It should be noted that this embodiment may not require a separate detector 270, as the detection protocol is managed by the controller 1900 as part of its self-monitoring, or self-aware operation. In this case, the detector 270 is considered to be a part of the controller 1900 rather than a separate unit as shown in FIG. 10. This self-aware capability is discussed more fully in co-pending U.S. patent application Ser. No. 15/242,693 filed Aug. 22, 2016. This patent application is incorporated by reference in its entirety.

A number of other embodiments are envisioned for the functioning of the malfunction detector 270 and recovery algorithm. In one embodiment, the malfunction situation is not actively detected, but the recovery algorithm is invoked regularly, as a maintenance or preventive measure. Accordingly the recovery algorithm is invoked as a preemptive measure to avoid the malfunctioning of the system. The recovery algorithm may be invoked at power up, for example, or after the detection of a predefined number of sort events, or the passage of a predefined quantity of sample fluid, or a predefined length of time. A distinguishing feature of this embodiment is that no actual detector may be required, but is instead replaced by a startup algorithm by controller 1900. In this case, as well as in the self-aware embodiment, no actual separate detector 270 may be required. In some embodiments, therefore, the detecting device may generate the signal that the recovery algorithm is to be invoked automatically at startup or at regular intervals.

In addition to the components described above, the MEMS particle sorting system 1000 shown in FIG. 10 may include a number of elements that may be helpful in implementing the recovery algorithm. The detector 270 shown in FIG. 10 may be an optical camera, for example, which monitors the position of the movable member 100. The camera may be triggered by a sort pulse coming from controller 1900 as a result of detecting the presence of a target particle by one of detectors 1300. The controller 275 may be a separate, dedicated pulse or waveform generator, or the functioning of controller 275 may be handled by computer 1900. However, other embodiments of the detector 270 are envisioned and described below.

In another embodiment an optical camera may be monitoring the motion of the movable number 110. The optical camera may be monitoring the field of view 240 shown in FIG. 9. When the camera determines that the motion of the movable member 110 has stopped, especially when triggered by a sort event, the camera may put out a signal to the controller 275 that the recovery algorithm needs to be applied.

In another embodiment, the detection mechanism 270 for the malfunctioning state is a sudden drop in purity or yield of the overall particle sorting performance. In this case, the detector 270 may detect a drop in yield, a drop in purity, or a change in fluid velocity or event rate. Any of these may indicate that the moveable member 110 is not moving properly. The malfunction detector 270 may put out a signal to the controller 275 that a malfunction has occurred and that the recovery algorithm should be invoked. In this case, the detector may be a software routine used by controller 1900.

Another embodiment of the detector 270 may measure the flow rate of the sort, that is the speed with which sort triggers are issued. When the detector measures that the frequency of sorts is too many or too few, the fluid flow may be anomalous. The detector may determine that a clog has occurred, and send the malfunction signal to the controller 275.

In yet another embodiment, the velocity of the particles passing by the laser interrogation region 140 may be monitored to detect a sudden drop in the velocity of the particles, which does not recover, may be an indication of the malfunctioning of the movable member 110.

In other embodiments an electrical, magnetic, acoustic, fluidic (pressure, e.g) or other measurement methodologies may be used to determine that the movable member 110 has become stuck. An acoustic signal, for example, may be at an audible frequency and may be detected when the movable member 100 has been freed and the movable member hits the stops on the substrate. Accordingly, in one embodiment, the recovery algorithm is applied until the acoustic signal is detected, indicating that the movable member 100 has been freed. Similarly, a back emf (electric-magnetic field) may be detected in the coil of the electromagnet 500, indicating that the movable member is once again moving freely. Accordingly, the detection device may rely on at least one of an optical signal, a camera, an electrical signal, a magnetic signal, an acoustic signal, and a deterioration in performance metrics to detect a malfunction.

These various embodiments are not meant to be an exhaustive list, but only to provide examples of the inventive concept. Embodiments other than those listed here are contemplated.

Figure 11:
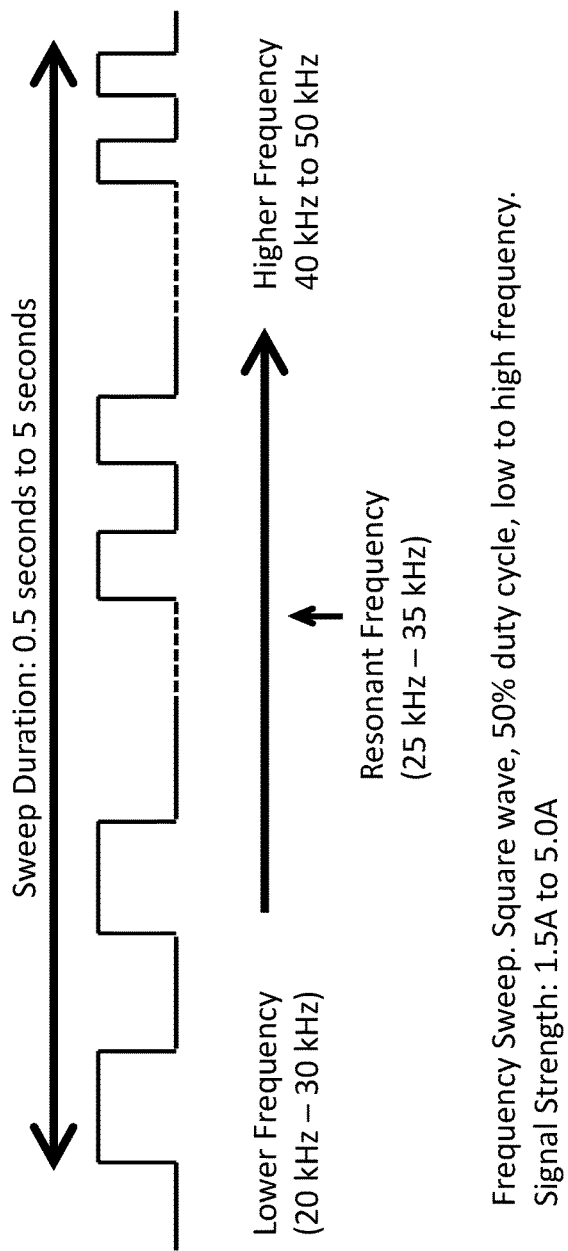
FIG. 11 is an illustration of an exemplary pulse train included in the recovery algorithm.

FIG. 11 is a schematic diagram of an exemplary embodiment of the pulse train generated by the controller 275 and delivered to the electromagnet 500 along line 2000. A corresponding motion is then imparted to the movable member 110 of the particle manipulation device 100. In this embodiment, a series of pulses may be sent to the electromagnet 500, which vary in frequency from a low frequency band of 20 kHz to a higher frequency band of 40 to 50 kHz ("chirp"). This range of frequencies may cover the resonant frequency of the particle manipulation device 100, which is in the range of 25 to 35 kHz. The total duration of this chirped pattern is anywhere from 0.5 seconds to five seconds long. The pulse train maybe a square wave, with 50% duty cycle and vary from low to high frequency as in a chirp. The signal strength maybe about 1.5 A to about 5 A, approximately. In other embodiments, the pulse train may be sinusoidal, triangular, or a ramp function for example, rather than a square wave.

The chirped pattern may be advantageous especially if it is centered on the expected resonant frequency of the movable member 100. The exact resonance may shift as a result of the clog or malfunction. The exact frequency will therefore depend on how the movable member 100 is constrained. The resonance may shift as the movable member is gradually freed. Therefore, chirping the pulse train over a range of frequencies is likely to excite a resonant mode, even if the frequency of this mode is changing. In other words, the multiple pulses delivered by controller 275 are designed to make use of the fact that the structure has a finite Q, and that the resonant frequency may shift during the application of the recovery algorithm.

Figure 12:
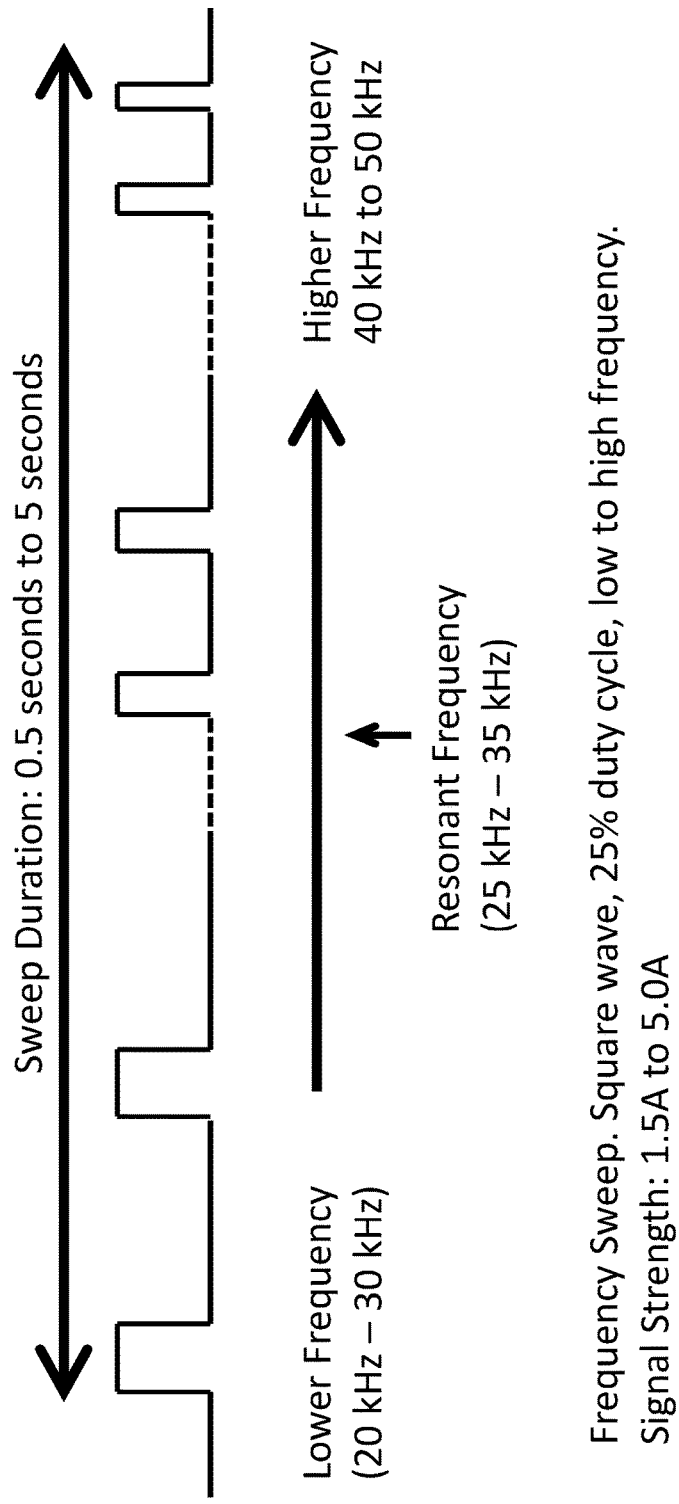
FIG. 12 an illustration of another exemplary pulse train included in the recovery algorithm.

FIG. 12 shows another embodiment of another pulse train which may be sent to the electromagnet 500. In this embodiment, the frequency is again chirped from a lower range of 20 kHz to 30 kHz to an upper range of 40 kHz to 50 kHz. The span of frequencies covers the resonant frequency of 25 kHz to 35 kHz of the movable member 110. In this embodiment, a square wave is again used, but with a 25% duty cycle. The reduced duty cycle may reduce the amount of heat generated within the unit. This may be important if the recovery algorithm is invoked frequently. As before, the duration of the chirp sweep is about 0.5 sec to about 5 seconds long.

It should be understood that other wave trains may be used other than a square wave. A sinusoidal, sawtooth or other more complex pattern may also be used.

Figure 13:
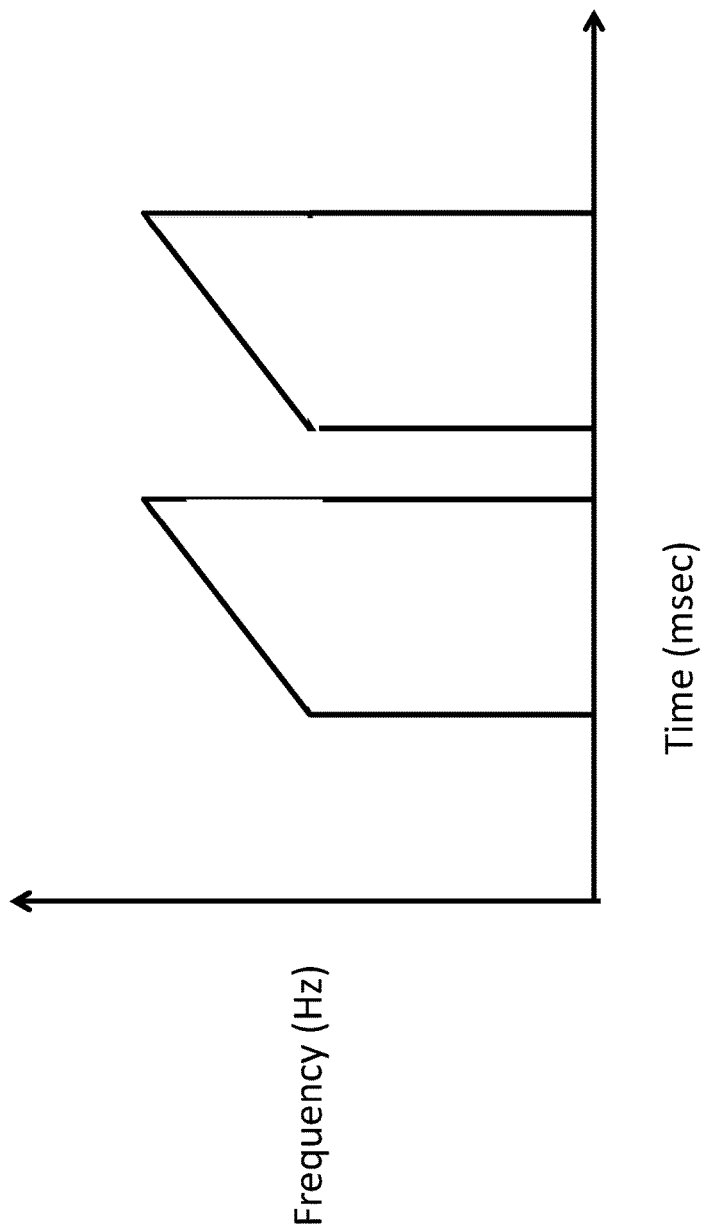
FIG. 13 is a representation of a chirp signal of the recovery algorithm.

FIG. 13 is a simplified schematic plot of the frequency versus time diagram of the chirp. As can be seen in FIG. 13, until the failure is detected, no pulse train is sent to the electromagnet 500. However, when a failure is detected, the chirped pattern is applied to the electromagnet 500. In this chirped pattern, a pulse train goes from the low range of about 20 kHz to the high range of about 50 kHz, during a period of a few seconds. The recovery algorithm then ceases briefly, the detector 270 is queried to see if the failure mode has been cleared, if not, the chirp is applied again to the electromagnet 500 as shown in FIG. 13.

Although the embodiments shown in FIGS. 1-13 are described with respect to an electromagnetic actuation mechanism, it should be understood that other actuation forces may be used instead. For example, if permeable features 116 and 130 are made from an electrically conductive rather than permeable magnetic material, a voltage potential may be placed across elements 116 and 130, producing an electrostatic force to move the movable member 110. Piezoelectric forces may also be used. In these cases, the recovery algorithm is similarly applied to the force-generating or motion-generating mechanisms in these other embodiments.

A method for using the system described above may include providing a microfabricated valve, detecting an interference of the movement of the particle sorting device, such that the device is malfunctioning, and generating a plurality of pulses that impart vibrational motion to the particle sorting device, wherein a waveform generator that generates the plurality of pulses. The plurality of pulses comprise at least one of a series of square waves, sinusoids may, trapezoid and ramps. In the method, at least one second pulse may follow within about 50 microseconds an initial pulse. The plurality of pulses may comprise a train of pulses with a range of frequencies. The range of frequencies may include a mechanical resonance frequency of the microfabricated particle sorting valve. The motion of the movable member may be amplified by resonant excitation by the plurality of pulses.

The description now turns to the fabrication of the devices shown in FIGS. 1-13. Fabrication may begin with the inlaid permeable features 116 and 130 formed in a first substrate. The substrate may be a single crystal silicon substrate, for example. To form these structures, depressions may be formed in these areas of the substrate surface by etching. First, photoresist may be deposited over the substrate surface and removed over the areas corresponding to 116 and 130. Then, the trenches may be formed by, for example, etching the substrate in potassium hydroxide (KOH) to form a suitable depression. A seed layer may be deposited conformally over the first substrate surface and patterned to provide the seed layer for plating NiFe into the trenches. The seed layer may be, for example, Ti/W or Cr/Au may then be deposited by sputtering, CVD or plasma deposition. This layer may be covered with photoresist and patterned according to the desired shape of the areas 116 and 130. Unwanted areas of photoresist and seed layer may then be removed by chemical etching. The permeable features may then be deposited over the patterned seed layer by sputtering, plasma deposition or electrochemical plating. It is known that permalloy (80% Ni and 20% Fe), for example, can readily be deposited by electroplating.

Alternatively, a liftoff method may be used to deposit a sheet of permeable material, most of which is then lifted off areas other than 116 and 130. Further details into the lithographic formation of inlaid, magnetically permeable materials may be found in, for example, U.S. Pat. No. 7,229,838. U.S. Pat. No. 7,229,838 is hereby incorporated by reference in its entirety. The substrate may then be planarized by chemical mechanical polishing (CMP), leaving a flat surface for the later bonding of a cover plate.

Having made the permeable features 116 and 130, the movable member or microfabricated valve 110 may be formed. The surface may again be covered with photoresist and patterned to protect the inlaid permeable features 116 and 130. The inlet channel 120 and output channels 122 and relieved area 144 may be formed simultaneously with the movable member 110 and 810. With movable member 110, 810 and other areas whose topography is to be preserved covered with photoresist, the features 110, 810, 120, 122 and 144 may be formed by deep reactive ion etching (DRIE) for example.

To form the fluidic channels, a cover plate may be bonded to the surface of the substrate which was previously planarized for this purpose. The cover plate may be optically transparent to allow laser light to be applied to the particles in the fluid stream flowing in the inlet channel 120, and for fluorescence emitted by the fluorescent tags affixed to the particles to be detected by the optical detection system described above. A hole formed in this transparent material may form the waste channel 142. Alternatively, a waste channel 142 may be formed in a second substrate, such as a second silicon substrate, and bonded to the surface of the first substrate. Alternatively, output channel 142 may be formed on the opposite surface of the first substrate using a silicon-on-insulator (SOI) substrate, with waste channel 142 and orifice 140 formed in the handle layer and dielectric layer of the SOI substrate, and the movable feature formed in the device layer.

Additional details for carrying out this process outlined above are well known to those skilled in the art, or readily found in numerous lithographic processing references.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A particle manipulation system comprising:
   a microfabricated particle sorting valve wherein the microfabricated particle sorting valve comprises silicon inlaid with a magnetically permeable material,
   a malfunction detecting device that detects an interference of the movement of the particle sorting device, such that when the microfabricated particle sorting valve is malfunctioning, the malfunction detecting device generates a signal indicating that a recovery algorithm is to be invoked; and
   a controller that is programmed to invoke the recovery algorithm and is coupled to an electromagnet, wherein a plurality of pulses from the controller to the electromagnet vibrate the microfabricated particle sorting valve by magnetic interaction with the electromagnet upon receiving the signal that the malfunction has occurred, wherein the malfunction is a state wherein the movable member no longer moves as designed in response to the controller, because of the interference.

2. The particle manipulation device of claim 1, further comprising:
   a particle of debris lodged in the microfabricated particle sorting valve, wherein vibration of the microfabricated particle sorting valve grinds the particle of debris into smaller pieces.

3. The particle manipulation system of claim 2, wherein the controller is programmed to generate at least one of a series of square waves, sinusoids, trapezoid and ramps and wherein the malfunction is interference of the movement of the microfabricated particle sorting valve; and wherein at least one second pulse follows within about 50 microseconds an initial pulse to vibrate the microfabricated particle sorting valve at a frequency to dislodge or grind debris and free the microfabricated particle sorting valve.

4. The particle manipulation system of claim 1, wherein the controller is programmed to generate a train of pulses with a range of frequencies.

5. The particle manipulation system of claim 1, wherein the the controller is programmed to vibrate the microfabricated particle sorting valve at a resonant frequency upon application of the plurality of pulses.

6. The particle manipulation system of claim 4, wherein the motion is amplified by resonant excitation by the plurality of pulses.

7. The particle manipulation system of claim 1, wherein the controller is programmed to generate a train of pulses with a range of frequencies beginning at a lower bound, and increasing in frequency to an upper bound, such that the pulse train is a chirp.

8. The particle manipulation system of claim 1, wherein the detecting device is programmed to generate the signal that the recovery algorithm is to be invoked automatically at startup or at regular intervals.

9. The particle manipulation system of claim 1, wherein the controller is programmed to generate a train of pulses with a range of frequencies beginning at an upper bound, and decreasing in frequency to a lower bound, such that the pulse train is a descending chirp.

10. The particle manipulation system of claim 1, wherein the detection device further comprises at least one of a camera, an electrical signal, a magnetic signal, an acoustic signal, and a signal based on deterioration in performance metrics to detect a malfunction.

11. The particle sorting system of claim 1, wherein the microfabricated valve comprises:
    a microfabricated, movable member formed on the substrate, and having a first diverting surface, wherein the movable member moves from a first position to a second position in response to a force applied to the movable member, wherein the motion is substantially in a plane parallel to the surface of the substrate;
    an sample inlet channel formed in the substrate and through which a fluid flows, the fluid including at least one target particle and non-target material, wherein the flow in the sample inlet channel is substantially parallel to the surface;
    a plurality of output channels into which the microfabricated member diverts the fluid, and wherein the flow in at least one of the output channels is substantially orthogonal to the plane, and wherein at least one output channel is located directly below at least a portion of the microfabricated member over at least a portion of its motion.

12. The micromechanical particle manipulation device of claim 1, wherein the plurality of output channels comprises a sort channel and a waste channel, wherein flow in the sort channel is substantially antiparallel to flow in the sample inlet channel, and wherein flow in the waste channel is substantially orthogonal to flow in the sample inlet channel and the sort channel.

13. The micromechanical particle manipulation device of claim 2, further comprising: a first permeable magnetic material inlaid in the movable member;
    a first stationary permeable magnetic feature disposed on the substrate; and
    a first source of magnetic flux external to the movable member and substrate on which the movable member is formed.

14. The micromechanical particle manipulation device of claim 5, wherein the movable member moves from the first position to the second position when the source of magnetic flux is activated.

15. A method for sorting particles with a microfabricated particle manipulation system, comprising:

providing a microfabricated particle sorting device, wherein the microfabricated particle sorting device comprises silicon inlaid with a magnetically permeable material;

detecting an interference of the movement of the microfabricated particle sorting device, such that when the microfabricated particle sorting device is malfunctioning a malfunction signal is generated wherein the malfunction is an interference of the microfabricated particle sorting device such that the microfabricated particle sorting device no longer moves as designed in response to a controller, because of the interference; and generating a plurality of pulses upon receiving the malfunction signal that impart vibrational motion to the particle sorting device, wherein the plurality of pulses vibrate the microfabricated particle sorting device by magnetic interaction with an electromagnet receiving the plurality of pulses.

16. The method of claim 15, wherein the plurality of pulses vibrates the microfabricated particle sorting valve at a frequency to dislodge or grind debris causing the interference and malfunction, and free the microfabricated particle sorting valve.

17. The method of claim 15, wherein at least one second pulse follows within about 50 microseconds an initial pulse.

18. The method of claim 15, wherein the plurality of pulses comprises a train of pulses with a range of frequencies.

19. The method of claim 15, wherein the range of frequencies includes a mechanical resonance frequency of the microfabricated particle sorting valve.

20. The method of claim 15, wherein the motion of the movable member is amplified by resonant excitation by the plurality of pulses.

* * * * *